United States Patent [19]

Newsome et al.

[11] Patent Number: 4,594,195

[45] Date of Patent: Jun. 10, 1986

[54] 5,6,7,8-TETRAHYDRO-NAPHONITRILE INTERMEDIATES

[75] Inventors: Peter M. Newsome, Cheam; Noel A. Mullan, Cranleigh; John P. Marshall, Lacey Green, all of England

[73] Assignee: Beecham Group p.l.c., England

[21] Appl. No.: 684,630

[22] Filed: Dec. 21, 1984

Related U.S. Application Data

[62] Division of Ser. No. 504,257, Jun. 14, 1983, Pat. No. 4,539,319.

[30] Foreign Application Priority Data

Jun. 16, 1982 [GB] United Kingdom ............... 8217452

[51] Int. Cl.⁴ .......................................... C07C 121/75
[52] U.S. Cl. ...................... 558/412; 544/59; 544/163; 544/398; 544/402; 546/205; 546/206; 556/417; 558/423
[58] Field of Search ....................... 260/465 R, 465 F; 556/417; 544/59, 163, 398, 402; 546/205, 206

[56] References Cited

U.S. PATENT DOCUMENTS 3,259,646  7/1966  Harris et al. ................... 260/465 F
4,391,731  7/1983  Boller et al. ................ 260/465 F X

OTHER PUBLICATIONS

Hagishita et al., J. Chem. Soc., Perkin Trans. 2, 59–67 (1978).

Primary Examiner—Dolph H. Torrence

Attorney, Agent, or Firm—Jacobs & Jacobs

[57] ABSTRACT

Compounds of formula (I)

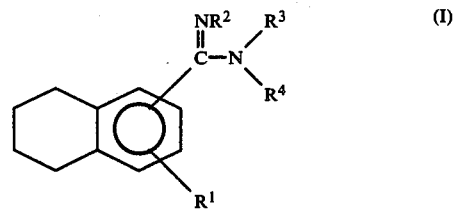

and acid addition salts thereof, wherein
$R^1$ is hydrogen, hydroxy, alkoxy, aryloxy, aralkoxy, heteroaryloxy or heteroaralkoxy; and
one of $R^2$, $R^3$ and $R^4$ is hydrogen and the others are the same or different and each is hydrogen, alkyl, aryl, aralkyl, heteroaryl or heteroaralkyl; or
$R^2$ is hydrogen and

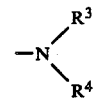

is mono- or
bi-cyclic amino, inhibit enterotoxin-induced secretion into the small intestine and are, therefore, useful in treating enterotoxin induced diarrhoea in humans and scours in animals.

6 Claims, No Drawings

6,5,7,8-TETRAHYDRO-NAPHONITRILE INTERMEDIATES

CROSS-REFERENCE

This is a division of Ser. No. 504,257 filed June 14, 1983, U.S. Pat. No. 4,539,319.

The present invention relates to novel amidine derivatives, to processes for their production and to their use in medicine. The invention also relates to novel intermediates and to processes for their production.

It has surprisingly been found that certain novel amidine derivatives inhibit enterotoxin-induced secretion into the small intestine and are, therefore, useful in treating enterotoxin induced diarrhoea in humans and scours in animals.

Accordingly, the present invention provides a compound of formula (I).

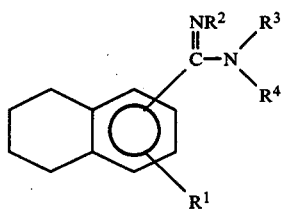
(I)

and acid addition salts thereof,
wherein
$R^1$ is hydrogen, hydroxy, alkoxy, aryloxy, aralkoxy, heteroaryloxy or heteroaralkoxy; and
one of $R^2$, $R^3$ and $R^4$ is hydrogen and the others are the same or different and each is hydrogen, alkyl, aryl, aralkyl, heteroaryl or heteroaralkyl; or
$R^2$ is hydrogen and

is mono- or bi-cyclic amino.
The groups $R^1$ and

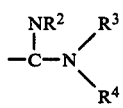

may each be located at any position of the benzene ring. Preferably they are located in the 1 and 4 positions, i.e. as shown in formula (IA).

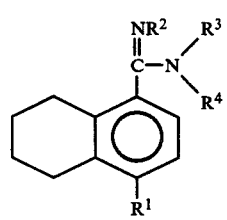
(IA)

Suitably the acid addition salts are pharmaceutically or veterinarily acceptable, but this is not essential as other salts may be useful in producing or purifying the desired compound of formula (I). Pharmaceutically and veterinarily acceptable acid addition salts include salts of hydrochloric, hydrobromic, hydroiodic, nitric, sulphuric, citric, lactic, maleic, pamoic and tartaric acids.

Suitable aryl groups for $R^2$, $R^3$ and $R^4$, and aryloxy groups for $R^1$ are those wherein the aryl moiety is optionally substituted phenyl or naphthyl.

Suitable aralkyl groups for $R^2$, $R^3$ and $R^4$, and aralkoxy groups for $R^1$ are those wherein the aryl moiety is optionally substituted phenyl or naphthyl and wherein the alkylene group is straight or branched and has from 1 to 6 carbon atoms.

Suitable alkyl groups for $R^2$, $R^3$ and $R^4$ and alkoxy groups for $R^1$ are those having straight, branched or cyclic alkyl moieties and are preferably chosen such that the total number of carbon atoms represented by alkyl moieties in $R^1$, $R^2$, $R^3$ and $R^4$ is 25 or less.

Suitable monocyclic amino groups

include those having a 5, 6 or 7-membered ring optionally containing one or two heteroatoms in addition to the nitrogen atom, which additional heteroatoms may be oxygen, nitrogen or sulphur.

Suitable bicyclic amino groups

include those having two fused rings wherein each ring has 5, 6 or 7 members, and optionally contain up to four heteroatoms, in addition to the nitrogen atom, which additional heteroatoms may be oxygen, nitrogen or sulphur.

The mono- and bi-cyclic amino groups described above may be aromatic or partially or fully saturated and may optionally be substituted.

Particularly suitable mono- and bi-cyclic amino groups include morpholino, thiomorpholino, piperazinyl and piperidinyl groups.

Suitable heteroaryloxy and heteroaralkoxy groups for $R^1$ include mono- or fused bicyclic aromatic groups containing up to four heteroatoms selected from oxygen, nitrogen and sulphur. Such heteroaryloxy and heteroaralkoxy groups may be optionally substituted. Suitably the alkylene group of such heteroaralkoxy groups is straight or branched and has from 1 to 6 carbon atoms.

The present invention also provides a process for producing compounds of formula (I) which process comprises reacting a compound of formula (II):

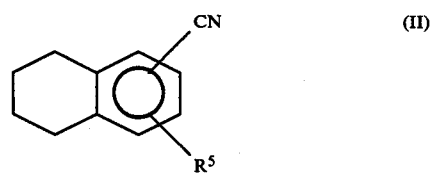
(II)

wherein $R^5$ is base-stable protected hydroxy or $R^1$ as defined in relation to formula (I) with the appropriate amino Grignard reagent of formula (III):

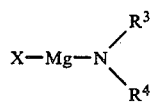

wherein X is halogen and optionally thereafter removing the protecting group if present and/or converting the compound of formula (I) into a further compound of formula (I) and if desired, forming an acid addition salt of the compound of formula (I) so produced.

As used herein the term "base-stable protected hydroxy" refers to a group which is stable under basic conditions but which can readily be converted to hydroxy under other conditions. Such groups are well known as are methods for their conversion to hydroxy. Suitable examples of base-stable protected hydroxy groups include benzyloxy and trialkylsilyloxy. The former may be converted to hydroxy by hydrogenation, the latter by treatment with acid.

The reaction of a compound of formula (II) with a compound of formula (III) may be effected under conventional conditions, for instance in an ether solvent at ambient or elevated temperature.

Conversion of one compound of formula (I) into another, and formation of salts may be effected by conventional methods.

Compounds of formula (II) are also novel.

Accordingly the present invention provides a compound of formula (II):

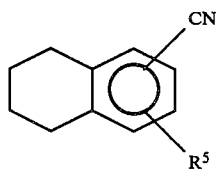

wherein $R^5$ is hydrogen, hydroxy, base-stable protected hydroxy alkoxy, aryloxy, aralkoxy, heteroaryloxy or heteroaralkoxy.

Suitably the compound of formula (II) has the cyano and $R^5$ groups in the 1 and 4 positions as shown in formula (IIA):

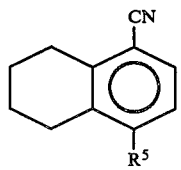

Suitable and preferred groups $R^5$ are as described above in relation to formula (I).

The present invention also provides a process for producing compounds of formula (II), which process comprises reacting a compound of formula (IV):

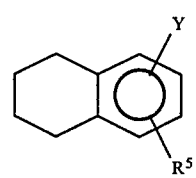

wherein $R^5$ is as defined in relation to formula (II) and Y is a halogen atom with an appropriate cyanide reagent and optionally thereafter converting the compound of formula (II) into a further compound of formula (II).

The reaction of a compound of formula (IV) with a cyanide may be effected by conventional methods and appropriate cyanide reagents are well known to the skilled person. The conversion of one compound of formula (II) into another may also be effected by conventional methods.

Compounds of formula (IV) are commercially available or may be produced by conventional methods.

Compounds of formula (I) inhibit enterotoxin-induced secretion into the small intestine, and are, therefore, useful in treatment of enterotoxin induced diarrhoea in humans and scours in animals, especially diarrhoea or scours caused by enteropathogenic strains of *Escherichia coli* which produce heat stable and/or heat labile enterotoxins. Related enterotoxins are produced by other enteropathogens, for example, cholera, and also cause diarrhoea which may also be treated using compounds of formula (I).

The present invention therefore provides a compound of formula (I) for use in human or veterinary medicine.

The present invention further provides a pharmaceutical or veterinary composition comprising a compound of formula (I) (hereinafter referred to as the "drug") and a pharmaceutically or veterinarily acceptable carrier therefor.

Pharmaceutical and veterinary compositions of the drug will, of course, be adapted for administration to the humans or animals to be treated. Thus, for example, the composition may be a shaped composition, such as a bolus, tablet or capsule. In such cases the pharmaceutically or veterinarily acceptable carrier will be chosen from the usual range of lubricants, dispersants, binders, fillers and the like. When these shaped compositions are for administration to cattle and pigs often they may for instance weigh at least 1 g, on occasions at least 2 g.

For administration to humans, especially children, the drug may suitably be presented as a syrup including suitable colouring and/or flavouring agents. Such syrups are conveniently presented in unit or multi-dose containers.

For veterinary use the composition may also be a dispersion or a solution of the drug in a suitable vehicle for use with an oral doser (this is a well known item of farm equipment, basically comprising a liquid reservoir, a mouthpiece adapted for insertion into animals mouths, and a pump mechanism whereby unit doses can be ejected from the reservoir through the mouthpiece). Conveniently the drug may be administered from an oral doser as an aqueous solution. Alternatively, the vehicle will be an oil or water based cream to ensure homogeneity of the unit doses administered.

The invention, therefore, also provides an oral doser containing a multi-dose of the drug in a veterinarily acceptable vehicle.

The drugs of the invention may also be added to the animal feed or drinking water. Thus the invention also provides animal feed or animal drinking water containing a compound of formula (I). It will be convenient to formulate these animal feed and drinking water compositions with a multi-dose of the drug so that the animal takes in an appropriate quantity of the drug along with its diet. It will also be convenient to present the composition of the invention as a pre-mix for addition to the feed or drinking water.

With human babies or young animals, a particularly useful technique is to blend their milk with the drugs of this invention.

The compositions of the invention may also be formulated for injection. In such cases the drug chosen is suitably dissolved in water for injection. Alternatively the drug may be administered in a solution used for parenteral fluid replacement therapy.

Often it will be appropriate to include in the compositions a further medicine such as an antibacterial agent for example an antibiotic such as amoxycillin or neomycin or a sulphonamide such as sulfadoxin, an agent to alter intestinal motility such as loperamide or a material such as pectin.

Treatment of diarrhoea and scours using the drug may be supplemented by oral rehydration therapy such as those described in U.K. Pat. No. 1,581,826 and German Offenlegungsschrift No. 28 54 281, U.K. Patent Application No. 2 012 163A, U.S. Pat. No. 3,898,328, Nalin, D. R. and Cash, R. A., *Bull. World Health Org.*, 43, 361 (1970), French Pat. No. 2 467 599, U.K. Pat. No. 1 465 308 and as described in "Secretory Diarrhoea", Ed M. Field, J. S. Fordtran and S. G. Schultz, American Physiological Society, Maryland, 1980 pp 179–185 and *Lancet*, (1975) pp 79 and 80. Conveniently the drug may be administered with the oral rehydration formulation.

Accordingly the present invention provides, in a particular aspect, a formulation for treating diarrhoea which comprises an effective non-toxic amount of a compound of formula (I) as hereinbefore defined and an oral rehydration composition comprising a pharmacologically acceptable aqueous solution containing at least 0.5% w/v of an actively absorbed monosaccharide, at least 25 mM sodium ions and having an osmolarity less than 500 m Osmolar.

Preferably the oral rehydration composition further comprises actively-absorbed amino acids and electrolytes.

The drug may be presented as a formulation containing one or more components of the oral rehydration composition for admixture with the remaining components.

Alternatively the drug may be provided separately and administered simultaneously or sequentially with the oral rehydration formulation.

The amount of drug administered must, of course, be sufficient to bring about the desired effect and will also depend on the body weight of the recipient and the chosen route of administration. Typical dosages are in the range from 0.1 to 100 mg/kg particularly from 1 to 10 mg/kg. Useful dosage units based on such dosage would contain from 0.1 mg to 5 g of the drug, more suitably 1 mg to 500 mg. Of course, it will be appreciated that many preferred compositions of the invention are in multi-dose form as, for the therapy of animals, it is often most desirable to be able rapidly to treat a number of animals. Such multi-dose compositions will contain, by way of example, at least 1 mg of the drug. Depending on the exact nature of the said multi-dose composition, often it will contain at least 50 mg of the drug, and on occasions as much as 50 g. Doses may be administered once or several times daily.

The present invention further provides a method for treating humans and animals, which method comprises administering an effective, non-toxic amount of a compound of formula (I) to the sufferer.

In a particular aspect the method of treatment comprises the administration of a pharmaceutical or veterinary composition of a compound of formula (I), as hereinbefore described.

The present invention will now be illustrated by the following Examples which are not intended to limit the invention in any way.

EXAMPLE 1

4-Bromo-1-methoxy-5,6,7,8-tetrahydronaphthalene (1)

5,6,7,8-Tetrahydro-1-naphthol (9.85 g, 66 mM), methyl iodide (30.6 g, 215 mM) and potassium carbonate (15 g, 90.8 mM) in acetone (500 ml) were heated under reflux with stirring for 3 days. The mixture was evaporated and the residue was extracted with 2M sodium hydroxide and ether. The organic layer was washed and dried to give 1-methoxy-5,6,7,8-tetrahydronaphthalene as as oil.

This oil was dissolved in dioxan (50 ml) and stirred as a biphasic mixture with potassium hydroxide (3.73 g, 66.5 mM) in water (20 ml). The mixture was cooled to ca. 5° C. and bromine (10.8 g, 67 mM) in dioxan (110 ml) was added over 1.5 hour. The residue was extracted with chloroform and water. The chloroform layer was dried and evaporated to give the bromide (1) as an oil 9.91 g (B.pt 107°–109° at 6 mmHg).

EXAMPLE 2

4-Methoxy-5,6,7,8-tetrahydro-4-naphthonitrile (2)

4-Bromo-1-methoxy-5,6,7,8-tetrahydronaphthalene (1) (2.5 g, 10.4 mM) cuprous cyanide (1.07 g, 5.4 mM), pyridine (1.5 ml) and hexamethylphosphoramide (0.3 ml) were stirred at 192° C. for 16 hours. The mixture was poured into aqueous ammonia and extracted with ether. The ether was washed with ammonia, water, dilute hydrochloric acid and then saturated brine. The ether solution was then dried and evaporated to give the nitrile (2) (1.90 g).

$^1$H nmr (CDCl$_3$): δ7.42 (d,1H), 6.68 (d,1H), 3.82 (s,3H), 2.88 (m,2H), 2.6 (m,2H), 1.77 (m,4H).

EXAMPLE 3

1-Benzyloxy-5,6,7,8-tetrahydronaphthalene (3)

5,6,7,8-tetrahydro-1-naphthol (5.9 g, 39 mM) was added to a suspension of potassium carbonate (8.3 g, 60 mM) in acetone (100 ml) and heated under reflux for 0.5 hour. Benzyl bromide (7.5 g, 43.8 mM) was then added and the mixture was heated under reflux for a further 3 days with stirring. The resulting suspension was filtered and the filtrate was evaporated under reduced pressure to give an oil. This oil was dissolved in ether, washed with water, dried (sodium sulphate) and evaporated to giving an oil which was distilled under high vacuum to give the benzyl ether (3) (9.4 g, b.p. 170°–176° C. at 0.8 mm Hg).

EXAMPLE 4

1-Benzyloxy-4-bromo-5,6,7,8-tetrahydronaphthalene (4)

A solution of potassium hydroxide (6.29 g, 112 mM) in water (40 ml) was added to 1-benzyloxy-5,6,7,8-tetrahydronaphthalene (22.75 g, 95.5 mM) dissolved in dioxan (25 ml). The resulting two phase system was stirred and maintained at 5°–8° C. whilst a solution of preformed bromine dioxan complex (bromine, 30.5 g, 191 mM in dioxan 125 ml) was added slowly over 1.5 hours. The reaction mixture was evaporated to give an oily solid which was extracted with chloroform. The chloroform solution was washed with water, dried (sodium sulphate) and evaporated to yield an oil (33.8 g). Half of this product was purified by column chromatography (alumina eluted with methylene chloride) to give the bromide (4) (10.3 g). Bpt 180°–195° C. at 0.4 mm Hg.

EXAMPLE 5

4-Benzyloxy-5,6,7,8-tetrahydro-4-naphthonitrile (5)

1-Benzyloxy-4-bromo-5,6,7,8-tetrahydronaphthalene (4.5 g, 14.2 mM), cuprous cyanide (1.71 g, 8.67 mM) pyridine (1 ml) and hexamethylphosphoramide (0.25 ml) was stirred at 170° C. for 16 hours. The resultant viscous mixture was dissolved in methylene chloride and washed with ammonium hydroxide solution, saturated brine solution, dried (sodium sulphate) and evaporated to give an oil (4.6 g). This oil was chromatographed on alumina (eluted with methylene chloride:-petroleum ether, 1:1) to give the nitrile (5) as a solid (2.4 g) m pt 74°–75.5° C.

EXAMPLE 6

4-Hydroxy-5,6,7,8-tetrahydro-1-naphthonitrile (6)

4-Benzyloxy-5,6,7,8-tetrahydro-1-naphthonitrile (0.6 g, 2.3 mM) was hydrogenated in ethanol (30 ml) in the presence of 10% palladium on charcoal catalyst (100 mg). After 2 hours the catalyst was filtered off and the filtrate was evaporated to give the phenol (6) a white solid (0.4 g) mpt 133°–134° C.

EXAMPLE 7

4-Isopropyloxy-5,6,7,8-tetrahydro-4-naphthonitrile (7)

4-Hydroxy-5,6,7,8-tetrahydro-4-naphthonitrile (1.73 g, 10 mm), isopropyl bromide (0.78 g, 10 mM), and sodium hydride (0.24 g, 10 mM) in dimethyl formamide were stirred for 3 hours. Water was added and the mixture was extracted with ether. The ether was dried and evaporated to give the isopropyl ether (7).

EXAMPLES 8 to 16

General amidine synthesis

The amine (1–4M) in ether (15 ml) was added to the Grignard reagent prepared from magnesium turnings (1.5M) and ethyl bromide (1.5M) in ether (20 ml). This mixture was heated at reflux for ½ hour and then the nitrile (1.0M) was added in either ether or benzene. The reaction was then heated under reflux for 3–4 days after which time the reaction was worked up by one of the following methods unless otherwise stated:

A. Aqueous ammonium chloride was added, the organic layer was then separated, dried and evaporated. The residue was treated with methyl formate, re-evaporated and then converted to the hydrochloride with ethanolic hydrochloric acid.

B. Aqueous ammonium chloride was added and the resulting suspension was filtered to give the required product.

C. Dilute hydrochloric acid was added and the resulting precipitate was collected.

EXAMPLE 8

1-[Imino(4-benzyloxy-5,6,7,8-tetrahydro-1-naphthyl)-methyl]-4-methylpiperazine, hydroiodide (8)

This was prepared from 4-benzyloxy-5,6,7,8-tetrahydro-1-naphthonitrile (1.32 g) and N-methylpiperazine (0.8 g) by the general amidine synthesis and worked up by method B to give 1-[imino(4-benzyloxy-5,6,7,8-tetrahydro-1-naphthyl)methyl]-4-methylpiperazine,hydroiodide (8) 1.0 g mpt 220° C. (recrystallised from aqueous ethanol).

EXAMPLE 9

4-methoxy-N',N'-di-n-propyl-5,6,7,8-tetrahydro-1-naphthamidine, hydrochloride (9)

This was prepared from 4-methoxy-5,6,7,8-tetrahydro-1-naphthonitrile (1.87 g) and di-n-propylamine (1 g) by the general amidine synthesis and worked up by method C to give 4-methoxy-N',N'-di-n-propyl-5,6,7,8-tetrahydro-1-naphthamidine, hydrochloride (9) 1.5 g.

EXAMPLE 10

1-[Imino(4-methoxy-5,6,7,8-tetrahydro-1-naphthyl)methyl]piperidine, hydrochloride (10)

This was prepared from 4-methoxy-5,6,7,8-tetrahydro-1-naphthonitrile (1.87 g) and piperidine (1.7 g) by the general amidine synthesis and worked up as follows: Dilute hydrochloric acid was added to the reaction mixture and the resulting oily aqueous layer was separated. This aqueous layer was basified with dilute sodium hydroxide and then extracted with chloroform. The chloroform extract was evaporated to give the amidine which was converted with hydrochloric acid to 1-[imino(4-methoxy-5,6,7,8-tetrahydro-1-naphthyl)-methyl]piperidine hydrochloride (10) 450 mg, m pt 256°–259° C.

EXAMPLE 11

N',N'-Di-n-butyl-4-methoxy-5,6,7,8-tetrahydro-1-naphthamidine, hydrochloride (11)

This was prepared from 4-methoxy-5,6,7,8-tetrahydro-1-naphthonitrile (1.65 g) and di-n-butylamine (1.7 g) by the general amidine synthesis and worked up by method A to give N',N'-dibutyl-4-methoxy-5,6,7,8-tetrahydro-1-naphthamidine, hydrochloride (11) 630 mg, m pt 224°–226° C. (recrystallised from butanol-methanol).

EXAMPLE 12

N',N'-Di-n-butyl-4-benzyloxy-5,6,7,8-tetrahydro-1-naphthamidine, hydrochloride (12)

This was prepared from 4-benzyloxy-5,6,7,8-tetrahydronaphthonitrile (2.63 g) and di-n-butylamine (1.88 g) by the general amidine synthesis and worked up by method A to give N',N'-Di-n-butyl-4-benzyloxy-5,6,7,8-tetrahydro-1-naphthamidine, hydrochloride (12) 540 mg m pt 253°–258° C. (d) (recrystallised from butanone-acetone).

EXAMPLE 13

4-Methoxy-N,N-di-amylamine-5,6,7,8-tetrahydro-1-naphthamidine, hydrochloride This was prepared from 4-methoxy-5,6,7,8-tetrahydronaphthonitrile (1.87 g) and di-amylamine (3.14 g) by the general amidine synthesis and worked up by method C to give 4-methoxy-N,N-di-amylamine-5,6,7,8-tetrahydro-1-naphthamidine, hydrochloride (13) 500 mg.

The di-amylamine was a mixture of isomers and afforded a mixture of isomers as product. These may be separated, for instance by hplc.

EXAMPLE 14

N',N'-di-n-butyl-4-isopropyloxy-5,6,7,8-tetrahydro-1-naphthamidine, hydrochloride (14)

This was prepared from 4-isopropyloxy-5,6,7,8-tetrahydro-1-naphthonitrile (2.15 g) and di-n-butylamine (2.6 g) by the general amidine synthesis and worked up by method C to give N',N'-di-n-butyl-4-isopropyloxy-5,6,7,8-tetrahydro-1-naphthamidine, hydrochloride (14) 950 mg, m pt 225°–228° C.

EXAMPLE 15

4-Benzyloxy-N',N'-dimethyl-5,6,7,8-tetrahydro-1-naphthamidine, hydrochloride (15)

This was prepared from 4-benzyloxy-5,6,7,8-tetrahydro-1-naphthonitrile (1.3 g) and dimethylamine (0.9 g) by the general amidine synthesis and worked up by method C to give 4-benzyloxy-N',N'-dimethyl-5,6,7,8-tetrahydro-1-naphthamidine, hydrochloride (15) 500 mg, m pt 225°–228° C. (recrystallised from water).

EXAMPLE 16

N',N'-di-n-butyl-4-hydroxy-5,6,7,8-tetrahydro-1-naphthamidine hydrochloride (16)

N,N-Di-n-butyl-4-benzyloxy-5,6,7,8-tetrahydro-1-naphthamidine hydrochloride (0.32 g, 0.7 mM) was hydrogenated in ethanol (20 ml) in the presence of 10% palladium on charcoal catalyst (0.07 g). After 1½ hours the catalyst was filtered off and the filtrate was evaporated to a dryness (0.3 g). This solid was triturated with acetone to give N',N'-di-n-butyl-4-hydroxy-5,6,7,8-tetrahydro-1-naphthamidine hydrochloride (16) 0.22 g, mp 233° C. (d).

BIOLOGICAL EVALUATION OF THE COMPOUNDS

1 Inhibition of enterotoxin induced secretion 7-9 day old infant mice are separated from their mothers shortly before use and are administered the compound 45 mins prior to oral challenge with 0.50 or 0.10 ml of partially purified heat stable enterotoxin prepared from a culture supernatant of an enteropathogenic strain of *E. coli*. Control animals receive drug vehicle 45 mins prior to challenge with a similar amount of culture filtrate. The compounds are administered orally to groups of at least 6 mice. Animals are killed two hours later and the entire intestine removed. The ratio of gut weight to remaining bodyweight (GW/BW) is determined from each animal and the increase in this ratio is determined by substracting 0.06 (GW/BW for untreated mice) from the GW/BW of the animal. Drug treated animals are compared with untreated controls. If the compound has had an effect in inhibiting the fluid secretion caused by the enterotoxin(s) present in the culture filtrate then the gut weight/bodyweight ratio should be reduced in the treated animals. The percentage fluid inhibition is determined from the formula:

$$\% \text{ inhibition} = 100 - [(100\Delta t)/\Delta c]$$

where $\Delta t$ = mean increase in GW/BW ratio for injected animals $\Delta c$ = mean increase in GW/BW ratio for control animals Results are given in Table 1 for a number of compounds tested against toxin from *E. coli* strain P16 (09:K103:H—:987P+). Experiments were also performed using toxins from other strains of *E. coli*. Results of these are shown in Table 2 and indicate a broad spectrum of anti-secretory activity.

2 Determination of Therapeutic Ratios (T.R.)

$LD_{50}$ determinations were made by dosing groups of suckling 8 day old mice with appropriate concentrations orally. Deaths were noted over a 7 day period and $LD_{50}s$ calculated using a probit regression program. $ED_{50}$ determinations were carried out by dosing groups of 6-8 day old mice with appropriate concentrations orally. The percentage fluid inhibition was determined as above and $ED_{50}s$ calculated using a log/linear regression analysis and the formula given in the British Pharmacopoeia.

For computation of T.R.'s the standard errors of $ED_{50}$ values were corrected to normalise the errors and the T.R.'s expressed as the ratio $LD_{50}/ED_{50}$ and standard eleviation range (Table 3).

TABLE 1

Activity of Compounds in 8 day old mice, challenged with ST from *E coli* P16.

| Compound of Example No. | Dose (mg/kg) | Route | % inhibition |
|---|---|---|---|
| 11 | 20 | p.o. | 59 |
|    | 10 | p.o. | 32 |
| 12 | 50 | p.o. | 70 |
|    | 20 | i.p. | 52 |
| 16 | 50 | p.o. | 58 |
|    | 20 | i.p. | 41 |
| 15 | 50 | p.o. | 39 |
|    | 10 | p.o. | 22 |
| 9  | 50 | p.o. | 43 |
|    | 10 | p.o. | 29 |
| 13 | 50 | p.o. | 38 |
|    | 10 | p.o. | 33 |
| 10 | 50 | p.o. | 33 |
|    | 10 | p.o. | 35 |
| 14 | 50 | p.o. | 52 |

All of the above compounds showed a statistically significant reduction of GW/BW ratio (at least p 0.05) as determined by the Students t test.

TABLE 2

Activity of the compound of Example 11 (20 mg/kg per os) in mice challenged with various *E coli* enterotoxins or with 8 Bromo cyclic GMP

| Secrettogogue | % inhibition |
|---|---|
| ST from *E coli* P16 | 59 |
| ST from *E coli* P155 | 31 |
| ST from *E coli* 431 | 47 |
| 8 Bromo cGMP (1µ mole/4 day old mouse) | 42 |

TABLE 3

Comparison of ED$_{50}$ and LD$_{50}$ of the compound of Example 11 in 8 day of mice.

| Compound of Example No. | ED$_{50}$ mg/kg | range | LD$_{50}$ mg/kg | range | ED$_{50}$/LD$_{50}$ |
|---|---|---|---|---|---|
| 11 | 16 | (11–18) | 87 | (83–91) | 5.6(3.9–8.1) |

3. Protection of Neonatal Mice from Lethal Enteropathogenic E. coli Infection 4 day old mice were orally dosed with 50 μl of phosphate buffered saline containing $1 \times 10^5$ organisms/ml of E. coli B44. The mice were then dosed b.i.d. with either placebo or drug for four days commencing 16 hours after infection. The animals were left with their mothers throughout this experiment and a daily record of deaths was made. The experiment was terminated when no mortality was seen over a 24 hour period. (Usually 7–10 days after infection). The mortality in the drug group was then compared with the mortality in the placebo group using the following formula:

% Reduction in mortality = $[(M_P - M_D)/M_P] \times 100$ where $M_P$ = mortality in group receiving placebo
$M_D$ = mortality in group receiving drug Statistical analysis was performed using 2×2 contingency tables (single tailed 'p'). Results are given in Table 4.

TABLE 4

| Days post infection | 2 | 3 | 4 | 5 | 6 | 7 |
|---|---|---|---|---|---|---|
| % mortality in mice dosed with Compound of Example 11 (10 mg/kg b.i.d.) (n = 60) | 25 | 47* | 53** | 57*** | 58** | 58** |
| % mortality in control mice (n = 62) | 31 | 68 | 79 | 84 | 84 | 84 |
| % Reduction in mortality | 18 | 31 | 33 | 32 | 30 | 30 |

*P < 0.05
**P < 0.01
***P < 0.001

Inhibition of Diarrhoea Induced by Enterotoxin Administration to Piglets

2–4 day old piglets were dosed with the compound orally 45 mins prior to oral challenge with 25 ml of culture filtrate prepared from an enteropathogenic E. coli strain P16. Control animals received drug vehicle 45 mins prior to challenge with a similar volume of toxin. Animals were observed for diarrhoea over a 7 hour period and the severity of scour scored on a 0 to 3 basis for each animal at hourly intervals. Results are given in Table 5.

TABLE 5

Inhibition by the compound of Example 11 of Enterotoxin Induced Scour in Piglets.

| Dose mg/kg | Mean scour score during 7 hr observation period ± SEM |
|---|---|
| 0 | *2.7 ± 0.1 |
| 25 | 2.1 ± 0.3 |
| 50 | *1.2 ± 0.2 |

*to*, p < 0.01, Students t

Formulation of the Compounds for Veterinary Administration

Formulation 1

Compound of Example 11, Bolus 100 mg

Boluses of the following composition were prepared:
Compound of Example 11—100 mg
Microcrystalline cellulose—500 mg
Corn starch—250 mg
Magnesium stearate—25 mg
Lactose, anhydrous—to 2500 mg The ingredients were passed through a 30 mesh stainless steel screen and blended in a suitable blender. The resultant compression mix was compressed directly on a tabletting machine to give tablets each containing 10 mg of the compound of Example 11.

Formulation 2

Oral Doser 1 mg/g

1 Kg of the following composition was prepared:

|  | % by wt. |
|---|---|
| Compound of Example 11 | 0.1 |
| Aluminium stearate | 6.0 |
| Sunflower oil to | 100 |

The aluminum stearate was dispersed with stirring in a portion of the sunflower oil heated to 115° C. The dispersion was added to the rest of the sunflower oil heated to 140° C. The gel was stirred at 130° C. for 15 minutes and then allowed to cool without stirring to room temperature. The milled compound of Example 11 was dispersed in the cooled gel base and then passed through a colloid mill to produce a fine, homogenous dispersion. The dispersion was filled into plastic bottles fitted with a dosing pump.

Formulation 3

Injection 5 mg/ml 1 liter of the following composition was prepared:

|  | % w/v |
|---|---|
| Compound of Example 11 | 0.5 |
| Sodium chloride | 0.5 |
| Water for injections to | 100 |

The amidine hydrochloride and sodium chloride were dissolved in the water for injections and the solution was filtered and filled into glass ampoules. The ampoules were sterilised by membrane filtration.

Formulation 4

Soluble Powder

1 Kg of the following composition was prepared:

|  | % by wt. |
| --- | --- |
| Compound of Example 11 | 3.6 |
| Lactose to | 100 |

The compound of Example 11 and lactose were sieved and mixed together in a suitable blender to give a homogenous powder. The powder was filled into jars. The powder was used at the rate 0.5 g per gallon of drinking water to medicate pigs.

Formulation 5

Oral Rehydration Formulation containing an amidine 1 kg of the following composition was prepared by mixing together the ingredients in dry powder form:
Glycine—10.3%
Dextrose (anhydrous)—67.6
Sodium Chloride—14.3
Potassium Dihydrogen Phosphate—6.8
Citric Acid—0.8
Tri-potassium Citrate—0.2
Compound of Example 11—0.15

60 g of the composition was then dissolved in 2 liters of water and fed to diarrhoeic calves.

Formulation 6

The following formulation may be prepared by the method set out below:
Compound of Example 11—0.3% w/v
Bentone 38 (1)—1.5% w/v i.e. 1.5 g/100 ml)
Propylene Carbonate—0.6% w/v
Pharmasorb (2)—10% w/v
Phosphoric Acid (3)—0.1% w/v
Ampicillin Trihydrate—6.0% w/v as free acid
Soya-Bean Oil—to 100%

(1) Bentone 38 is dimethyl dioctadecyl 125 hectorite, $[Mg_8LiSi_{12}O_{30}(OH)_6]^{\ominus}[(CH_3)_2N(C_{18}H_{37})_2]^{\oplus}$ (2) Pharmasorb is a brand of activated Attapulgite,
(3) The phosphoric acid is present in the minor proportion to balance the alkaline pH of the Bentone.

The Bentone was dispersed in the soya-bean oil, and when thoroughly distributed, the propylene carbonate was added with high speed mixing, followed by colloid milling to produce the base. Into this base was first mixed the phosphoric acid, and then the pharmasorb, the penicillin, and the amidine and the resultant suspension was then passed through a colloid mill once more.

We claim:

1. A compound of formula (II)

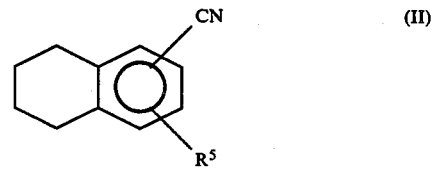

wherein $R^5$ is hydroxy, base stable protected hydroxy, alkoxy, aryloxy, aralkoxy, heteroaryloxy or heteroaryl $C_{1-6}$ alkyloxy wherein the heteroaryl moiety is a mono- or fused bicyclic aromatic group containing up to 4 heteroatoms selected from oxygen, sulphur and nitrogen.

2. A compound as claimed in claim 1 wherein the $R^5$ group is in the 1-position and the CN group is in the 4-position.

3. The compound of claim 1 which is 4-methoxy-5,6,7,8-tetrahydro-4-naphthonitrile.

4. The compound of claim 1 which is 4-benzyloxy-5,6,7,8-tetrahydro-4-naphthonitrile.

5. The compound of claim 1 which is 4-hydroxy-5,6,7,8-tetrahydro-1-naphthonitrile.

6. The compound of claim 1 which is 4-isopropyloxy-5,6,7,8-tetrahydro-4-naphthonitrile.

* * * * *